(12) United States Patent
Isern et al.

(10) Patent No.: US 10,124,053 B2
(45) Date of Patent: Nov. 13, 2018

(54) VACCINES AND METHODS FOR CREATING A VACCINE FOR INDUCING IMMUNITY TO ALL DENGUE VIRUS SEROTYPES

(71) Applicants: Sharon Isern, Estero, FL (US); Scott F. Michael, Estero, FL (US)

(72) Inventors: Sharon Isern, Estero, FL (US); Scott F. Michael, Estero, FL (US)

( * ) Notice: Subject to any disclaimer, the term of this patent is extended or adjusted under 35 U.S.C. 154(b) by 0 days.

(21) Appl. No.: 15/413,347

(22) Filed: Jan. 23, 2017

(65) Prior Publication Data

US 2017/0202945 A1    Jul. 20, 2017

Related U.S. Application Data

(63) Continuation of application No. 13/660,653, filed on Oct. 25, 2012, now abandoned.

(60) Provisional application No. 61/550,982, filed on Oct. 25, 2011.

(51) Int. Cl.
| | |
|---|---|
| *A61K 39/12* | (2006.01) |
| *A61K 39/00* | (2006.01) |
| *C12N 7/00* | (2006.01) |
| *C12Q 1/70* | (2006.01) |
| *C12N 15/62* | (2006.01) |
| *C07K 14/005* | (2006.01) |

(52) U.S. Cl.
CPC ............ *A61K 39/12* (2013.01); *C07K 14/005* (2013.01); *C12N 7/00* (2013.01); C07K 2319/40 (2013.01); C12N 2770/24122 (2013.01); C12N 2770/24134 (2013.01); C12N 2770/24151 (2013.01)

(58) Field of Classification Search
CPC .............. C07K 14/005; C07K 2319/00; C12N 2770/24122; C12N 2770/24134; A61K 39/12
See application file for complete search history.

*Primary Examiner* — Barry A Chestnut
(74) *Attorney, Agent, or Firm* — Robert Varkonyi; Zagrebelsky Law P.A.; Michele Lawson

(57) ABSTRACT

Described here is a method to produce a chimeric protein having portions of yellow fever virus and dengue virus. A small portion of the yellow fever virus 17D vaccine strain envelope protein (or other related flavivirus) can be replaced by the corresponding portion from the dengue virus envelope protein. In some embodiments the chimeric protein may be used to create a treatment composition for DENV infection. In others, the chimeric protein may be used to create a vaccine that will induce broadly protective antibodies against dengue virus and reduce the induction of non-neutralizing antibodies that will cause enhancement.

13 Claims, 20 Drawing Sheets

Specification includes a Sequence Listing.

| | 4.8A | D11C$_{KL}$ | 1.6D |
|---|---|---|---|
| DENV1 | 6.70175E-10 | 3.95E-10 | 2.75125E-10 |
| DENV2 | 7.5382E-10 | 1.8205E-09 | 1.86987E-09 |
| DENV3 | 1.43508E-09 | 3.293E-10 | 1.7884E-09 |
| DENV4 | 1.15297E-09 | 4.7165E-10 | 1.619E-09 |

Dengue/yellow fever E protein alignment

```
              1                                                              >DI/II
ConsDENV4E   MRCVGVGNRD FVEGVSGGAW VDLVLEHGGC VTTMAQGKPT LDFELTKTTA KEVALLRTYC
IEASISNITT   ConsDENV3E MPCVGVGNRD FVEGLSGATW VDVVLEHGGC VTTMAKNKPT LDIELQKTEA
TQLATLRKLC   IEGKITNITT ConsDENV2E [XXX]IG[XXX] [X]VEGVSGGSW VDIVLEH[XX] V[X]TMAKNKPT
L[XX][X]KTEA KQPATLRKYC IEAKLTNTT[X] ConsDENV1E MRCVGIGSRD FVEGLSGATW VDVVLEHGSC
VTTMAKDKPT   LDIELLKTEV TNPAVLRKLC IEAKISNTTT YFV17DE    AHCIGITDRD FIEGVHGGTW
VSATLEQDKC   VTVMAPDKPS LDISLETVAI DRPAEVRKVC YNAVLTHVKI 71                                                             >DII/I
ConsDENV4E   ATRCPTQGEP YLKEEQDQQY ICPRDVVDR[X] [XXXXLF]K  GGVVTCAKFS CSGKITGNLV
QIENLEYTVV   ConsDENV3E DSRCPTQGEA XLPEEQDQNY VCKHTYVDR[X] [XXXLF]R  GSLVTCAKFQ
CLEPIEGKVV   QYENLKYTVI ConsDENV2E [XX]RCPT[XXX] [X]LNEEQDKRF VCKH[XX]DR[X] [XXXLF]K
[XXX]AMFT   CKKNMEGKXV QPENLEYTIV ConsDENV1E DSRCPTQGEA TLVEEQDANF VCRRTFVDR[X]
[XX]K       GSLITCAKFK CVTKLEGKIV QYENLKYSVI YFV17DE    NDKCPSTGEA HLAEENEGDN
ACKRTYSDR[X] [XXXLF]K  GSIVACAKFT CAKSMSLFEV DQTKIQYVIR 141                                                            >DI/II
ConsDENV4E   VTVHNGD[X]HA VGNDTSN[XX]V TATITPRSPS VEVKLPDYGE LTLDCEPRSG IDFNEMILMK
MKKKTWLVHK   ConsDENV3E ITVRTGDEHQ VGNET---[X]V TAEITPQAST TEAILPEYGT LGLECSPRTG
LDFNEMILLT   MKNKAWMVHR ConsDENV2E I[XXXXXX][X] VGND[XXX][X]K EIKITPQSSI TEAELTGYGT
VTMECSPRTG   LDFNEMVLLQ MEKKAWLVRR ConsDENV1E VTVHTGDQHQ VGNESTE[XX]T TATITPQAPT
XEIQLTDYGA   LTLDCSPRTG LDFNEMVLLT MKEKSWLVHR YFV17DE    AQLHVGAKQE NWNTDIK[X]-
TLKFDALSGS   QEVEFIGYGK ATLECQVQTA VDFGNSYIAE METESWIVDR 211
ConsDENV4E   QWFLDLPLPW TAGADTSEVH WNYKERMVTF KVPHAKRQDV TVLGSQEGAM HSALAGATEV
DSGDGNH--    ConsDENV3E QWFFDLPLPW TSGATTETPT WNRKELLVTF KNAHAKKQEV VVLGSQEGAM
HTALTGATEI   QNSGGTS--  ConsDENV2E QWFLDLPLPW LPGADTQGSN WIQKETLVTF K[XXXXXX]DV
VVLGSQEGAM   HTALTGATEI QMSSGNL--  ConsDENV1E QWFLDLPLPW TSGASTSQET WNRQDLLVTF
KTAHAKKQEV   VVLGSQEGAM HTALTGATEI QTSGTTT--  YFV17DE    QWAQDLTLPW QSG---SGGV
WPEMHHLVEF   EPPHAATIRV LALGNQEGSL KTALTGAMRV TKDTNDNNLY 281 >DII/I            >DI/DIII
ConsDENV4E   -MFAGHLKCK VRMEKLRIKG MSYTMCSGKF SIDKEMAETQ HGTTVVKVKY [X]GAGAPCKVP
IEIRDVNKEK   ConsDENV3E -IFAGHLKCR LRMDKLELKG MSYAMCTNTF VLKKEVSETQ HGTILIKVEY
[X]GEDXPCKIP FSTEDGQGKA ConsDENV2E -LFTGHLKCR LRMDKLQLKG MSYSMCTGK[X] [XXX]KE[X]AETQ
[XXX]VIR[XX] [X]GDGSPCK[X]P [XX]MDLEKRH ConsDENV1E -IFAGHLKCR LKMDKLTLKG MSYVMCTGSF
KLEKEVAETQ   HGTVLVQIKY [X]GTDAPCKIP FSTQDEKGVT YFV17DE    KLHGGRVSCP VKLSALTLKG
TSYKICTDKM   FFVKNPTDTG HGTVVMQVKV [X]SKGAPCRIP VIVADDLTAA 351
ConsDENV4E   VV-GRVISST PLAENTNSVT NIELEPPFGD SYIVIGVGNS ALTLHWFRKG SSIGKMFEST
YRGAKRMAIL   ConsDENV3E HN--GRLITAN PVVTKKEEPV NIEAEPPFGE SNIVIGIGDN ALKINWYKKG
SSIGKMFEAT   ARGARPMAIL ConsDENV2E VL-G[XXX]VN [X]VTER[XXX] N[XXXX]PFGD SY[XX]GVEPG
C[X][XXXXXX]G SSIGQMFETT MRGAKRMAIL ConsDENV1E QN-GRLITAN PIVTDKEKPV NIEAEPPFGE
SYIVIGAGEK   ALKLSWFKKG SSIGKMFEAT ARGARRMAIL YFV17DE    INKGILVTVN PIASTNDDEV
LIEVNPPFGD   SYIIVGRGDS RLTYQWHKEG SSIGKLFTQT MKGVERLAVM
```

FIG. 13

```
            421
ConsDENV4E  GETAWDFGSV  GGLFTSLGKA  VHQVFGSVYT  TMFGGVSWMI  RILIGFLVLW  IGTNSRNTSM
AMTCIAVGGI  ConsDENV3E  GDTAWDFGSV  GGVLNSLGKM  VHQIFGSAYT  ALFSGVSWVM  KIGIGVLLTW
IGLNSKNTSM  SFSCIAIGII  ConsDENV2E  GDTAWDFGSL  GGVFTSIGKA  LHQVFGAIYG  AAFSGVSWTM KILIGVIITW  IGMNSRSTSL  SVSLVLVGVV  ConsDENV1E  GDTAWDFGSI  GGVFTSVGKL  VHQIFGTAYG
VLFSGVSWTM  KIGIGVLLTW  LGLNSRSTSL  SMTCIAVGLV  YFV17DE     GDTAWDFSSA  GGFFTSVGKG
IHTVFGSAFQ  GLFGGLNWIT  KVIMGAVLIW  VGINTRNMTM  SMSMILVGVI 491
ConsDENV4E
TLFLGFTVQA
ConsDENV3E
TLYLGAVVQA
ConsDENV2E
TLYLGVMVQA
ConsDENV1E
TLYLGVMVQA
YFV17DE
MMFLSLGVGA
```

▓▓ = Fusion Loop
Bold and Underlined = Within 5A of Fusion Loop
▓▓ = Within 14A of Fusion Loop (shown only for DENV2)
▓▓ = Loss of binding position for 4.8A, D11Ck1, and 1.6D

VACCINES AND METHODS FOR CREATING A VACCINE FOR INDUCING IMMUNITY TO ALL DENGUE VIRUS SEROTYPES

CROSS-REFERENCE TO RELATED APPLICATION

This application is a continuation of U.S. Nonprovisional patent application Ser. No. 13/660,653, filed Oct. 25, 2012, and which claims priority to and the benefit of U.S. Provisional Patent Application No. 61/550,982, filed on Oct. 25, 2011, and is incorporated herein by reference in its entirely.

GOVERNMENT SUPPORT

This invention was made with government support under cooperative agreements awarded by grant no. HDTRA1-10-1-0009 from the Defense Threat Reduction Agency. The government may have certain rights to the invention.

BACKGROUND OF THE INVENTION

Dengue viruses (DENV), members of the genus *Flavivirus*, are the most common cause of mosquito-borne viral diseases in tropical and subtropical regions around the world. Approximately 50 to 100 million people per year are infected with DENV. DENV infections may be asymptomatic, but most often manifest as dengue fever (DF), a self-limited disease. Dengue hemorrhagic fever (DHF) and dengue shock syndrome (DSS) are more severe, life-threatening manifestations of dengue infection. DENV imposes one of the largest social and economic burdens of any mosquito-borne viral pathogen. There is no specific treatment for infection, and control of dengue virus by vaccination has proved elusive. The pathogenesis of DHF/DSS is not completely understood. There are four serotypes of dengue virus (DENV-1, DENV-2, DENV-3, and DENV-4). Infection with one serotype confers lifelong homotypic immunity, but only short term (approximately three to six months) cross protection against heterotypic serotypes.

The risk of severe disease is greatest during secondary, heterotypic infections in subjects with more than one circulating serotype. There is evidence that prior infection with one type can produce an antibody response that can intensify, or enhance, the course of disease during a subsequent infection with a different serotype. The possibility that vaccine components could elicit enhancing antibody responses, as opposed to protective responses, has been a major concern in designing and testing vaccines to protect against dengue infections. There is thus a need for a vaccine that may be effective against different serotypes and which does not enhance the course of the DENV infection.

SUMMARY OF THE INVENTION

Described here is a method of forming a chimeric protein, comprising the steps of providing a yellow fever virus 17-D envelope protein having SEQ ID No. 1; providing a dengue fever virus envelope protein selected from the group consisting of SEQ ID No. 2, SEQ ID No. 3, SEQ ID No. 4, or SEQ ID No. 5; and substituting one or more of amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of SEQ ID No. 1 with the corresponding amino acid of the selected dengue fever virus envelope protein to create a chimeric envelope protein.

Also described here is a method of creating a treatment composition, comprising the steps of providing a portion of an envelope protein from a *flavivirus*; providing a dengue fever virus envelope protein selecting from the group consisting of SEQ ID No. 2, SEQ ID No. 3, SEQ ID No. 4, or SEQ ID No. 5; substituting a portion of the envelope protein amino acids of the *flavivirus* with a the corresponding envelope protein amino acids of the selected dengue fever virus to create a chimeric envelope protein; providing a pharmaceutically acceptable excipient; and mixing the chimeric envelope protein and the excipient.

Further described here is a chimeric protein, comprising: an envelope protein comprised of yellow fever virus 17-D envelope protein having SEQ ID No. 1, wherein selected amino acids of the yellow fever virus 17-D envelope protein are substituted with corresponding amino acids of dengue fever virus envelope protein selected from the group consisting of SEQ ID No. 2, SEQ ID No. 3, SEQ ID No. 4, or SEQ ID No. 5.

Also described here is a composition for treatment of dengue fever virus, comprising: a chimeric envelope protein comprised of a *flavivirus* envelope protein, wherein selected amino acids of the *flavivirus* envelope protein are substituted with corresponding amino acids of dengue fever virus envelope protein selected from the group consisting of SEQ ID No. 2, SEQ ID No. 3, SEQ ID No. 4, or SEQ ID No. 5; and a pharmaceutically acceptable excipient.

BRIEF DESCRIPTION OF THE DRAWINGS

FIG. 13 shows an amino acid sequence alignment of DENV-1 to 4 and the yellow fever 17-D envelope protein.

DETAILED DESCRIPTION OF THE INVENTION

Figure 1A:
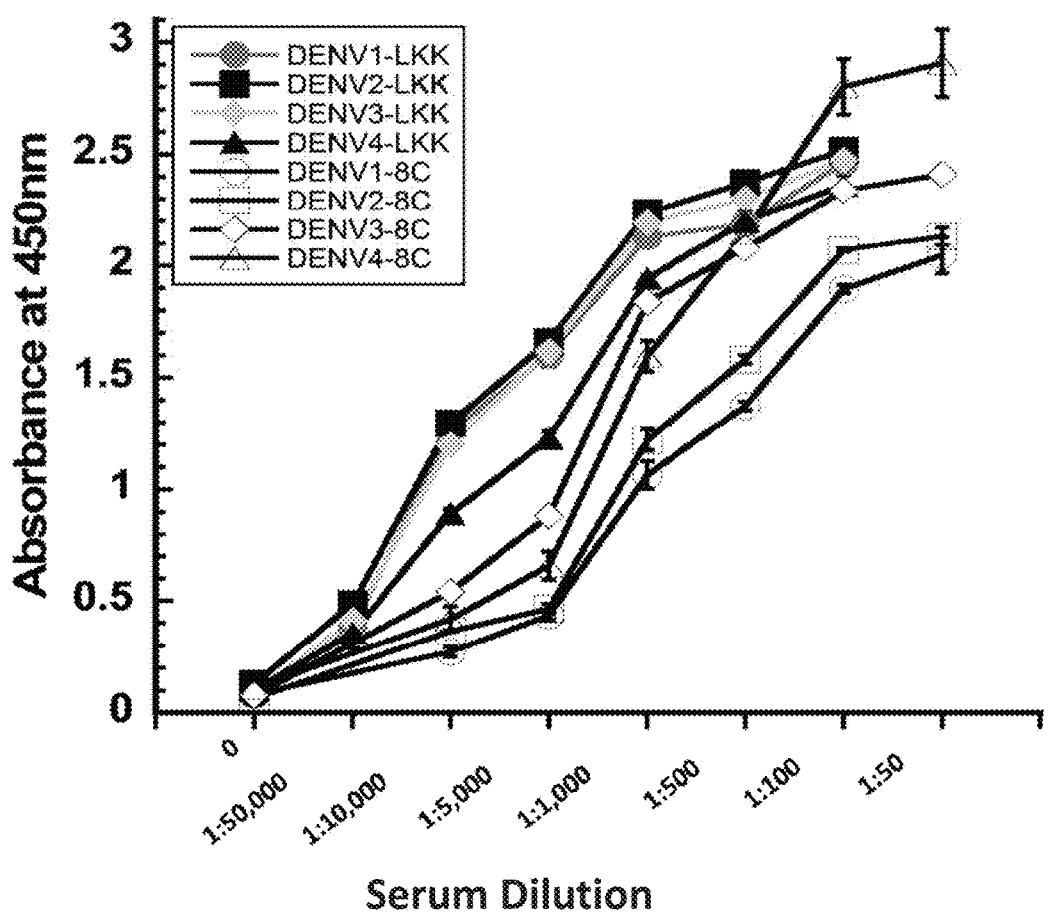
FIG. 1A shows the results of ELISA assays with immobilized virus envelope glycoproteins, patient sera, and monoclonal antibodies from DENV infected patients at various dilutions.

An increasing problem for public health officials has been the occurrence of severe complications arising from dengue viral infection. Both dengue hemorrhagic fever (DHF) and shock syndromes (DSS) are clinical outcomes related to the presence of pre-existing immunity to a heterologous dengue virus serotype. Dengue Haemorrhagic Fever is initially characterized by a minor febrile illness lasting 3-5 days. The patient may deteriorate at defervescence into the next phase of the syndrome with hemostatic disorders, and increased vascular permeability frequently accompanied by internal bleeding and shock. As many as 1.5 million children are reported to have been hospitalized with 33,000 deaths from this syndrome since it was first recognized in Thailand (World Health Organization 1989). DHF/DSS has since continued to persist, and outbreaks can pose major problems to public health in many countries.

Dengue virus (DENV) is a mosquito-transmitted virus and is expanding in geographic range and also in disease severity. There are four distinct serotypes of dengue that cause similar disease symptoms, serotypes 1-4. Infection with a single serotype results in an immune response that is protective against that same serotype, but causes a cross-reactive antibody response against the other serotypes (and other flaviviruses as well). Epidemiological studies have shown that the presence of cross-reactive antibodies correlates with a more severe disease outcome during subsequent infections with a different serotype. The mechanism for this effect appears to be an antibody-dependent enhancement of infection of macrophage and macrophage like cells that express Fc receptors. These cells are normally not infected efficiently by dengue, but become highly infectable in the presence of dengue virus binding antibodies that then target the virus particles directly to the macrophages through the interaction of the antibody heavy chains and the cellular Fc receptors.

Studies have attempted to determine the human antibody response against dengue virus by characterizing human anti-dengue monoclonal antibodies. Prior to this work, most immunological studies on dengue infections had been conducted in mice, which are not a natural host for dengue and which produce a very different antibody response. One of the conclusions to come out of the human studies is that the dominant human antibody response against the dengue virus surface proteins, membrane (prM and M) and envelope (E, soluble envelope protein, sE), is non-neutralizing and cross reactive against the four serotypes of dengue. These non-neutralizing, cross-reactive antibodies are the primary cause of the antibody dependent enhancement of disease. This presents problems for the development of a dengue vaccine that uses the entire prM and E proteins. Even if a vaccine formulation using full length prM and E can induce a broad neutralizing response against all four serotypes, when the neutralizing antibody response wanes over time, the dominant non-neutralizing response will remain and prime vaccine recipients for severe disease if they are ever infected again. It is not yet clear how long the neutralizing vaccine response would endure or when vaccine recipients might become at risk for disease enhancement, but there are few examples of vaccines that induce lifelong protection.

The invention relates to a chimeric protein and methods for producing a chimeric protein for immunizing an individual against dengue and dengue clinical outcomes, and for treating an individual susceptible to infection or infected with dengue virus. In some embodiments, the chimeric protein could be used to create a treatment composition for an infected individual, while in others the chimeric protein could be used to produce a live attenuated vaccine, or a subunit vaccine that is not replicative.

The chimeric protein is created by substituting a portion of yellow fever virus (YFV) envelope protein, *Flavivirus yellow fever virus*, with a portion of any of the strains of dengue virus (DENV) envelope protein, *Flavivirus dengue virus*. In one embodiment, the chimeric protein of the invention is created using YFV 17D strain envelope protein. Although the example is limited to YFV envelope protein, in other embodiments it is envisioned the chimeric protein may be created using the envelope protein of any *flavivirus*, for example West Nile Virus, St. Louis encephalitis, Dengue Fever virus, Japanese encephalitis, and Kunjin virus, and substituting any of the four strains of DENV envelope protein.

YFV 17D strain envelope protein has the following sequence, identified as SEQ ID No. 1:

AHCIGITDRDFIEGVHGGTWVSATLEQDKCVTVMAPDKPSLDISLETVAI

DRPAEVRKVCYNAVLTHVKINDKCPSTGEAHLAEENEGDNACKRTYSDRG

WGNGCGLFGKGSIVACAKFTCAKSMSLFEVDQTKIQYVIRAQLHVGAKQE

NWNTDIKTLKFDALSGSQEVEFIGYGKATLECQVQTAVDFGNSYIAEMET

ESWIVDRQWAQDLTLPWQSGSGGVWREMHHLVEFEPPHAATIRVLALGNQ

EGSLKTALTGAMRVTKDTNDNNLYKLHGGHVSCRVKLSALTLKGTSYKIC

TDKMFFVKNPTDTGHGTVVMQVKVSKGAPCRIPVIVADDLTAAINKGILV

TVNPIASTNDDEVLIEVNPPFGDSYIIVGRGDSRLTYQWHKEGSSIGKLF

-continued
TQTMKGVERLAVMGDTAWDFSSAGGFFTSVGKGIHTVFGSAFQGLFGGLN

WITKVIMGAVLIWVGINTRNMTMSMSMILVGVIMMFLSLGVGA

DENV strain 1 envelope protein has the following sequence, identified as SEQ ID No. 2:

MRCVGIGSRDFVEGLSGATWVDVVLEHGSCVTTMAKDKPTLDIELLKTEV

TNPAVLRKLCIEAKISNTTTDSRCPTQGEATLVEEQDANFVCRRTFVDRG

WGNGCGLFGKGSLITCAKFKCVTKLEGKIVQYENLKYSVIVTVHTGDQHQ

VGNESTEHGTTATITPQAPTXEIQLTDYGALTLDCSPRTGLDFNEMVLLT

MKEKSWLVHKQWFLDLPLPWTSGASTSQETWNRQDLLVTFKTAHAKKQEV

VVLGSQEGAMHTALTGATEIQTSGTTTIFAGHLKCRLKMDKLTLKGMSYV

MCTGSFKLEKEVAETQHGTVLVQIKYEGTDAPCKIPFSTQDEKGVTQNGR

LITANPIVTDKEKPVNIEAEPPFGESYIVIGAGEKALKLSWFKKGSSIGK

MFEATARGARRMAILGDTAWDFGSIGGVFTSVGKLVHQIFGTAYGVLFSG

VSWTMKIGIGVLLTWLGLNSRSTSLSMTCIAVGLV TLYLGVMVQA

DENV strain 2 envelope protein has the following sequence, identified as SEQ ID No. 3:

MRCIGISNRDFVEGVSGGSWVDIVLEHGSCVTTMAKNKPTLDFELIKTEA

KQPATLRKYCIEAKLTNTTTESRCPTQGEPSLNEEQDKRFVCKHSMVDRG

WGNGCGLFGKGGIVTCAMFTCKKNMEGKXVQPENLEYTIVITPHSGEEHA

VGNDTGKHGKEIKITPQSSITEAELTGYGTVTMECSPRTGLDFNEMVLLQ

MEXKAWLVHRQWFLDLPLPWLPGADTQGSNWIQKETLVTFKNPHAKKQDV

VVLGSQEGAMHTALTGATEIQMSSGNLLFTGHLKCRLRMDKLQLKGMSYS

MCTGKFKXVKEIAETQHGTIVIRVQYEGDGSPCKIPFEIMDLEKRHVLGR

LITVNPIVTEKDSPVNIEAEPPFGDSYIIIGVEPGQLKLNWFKKGSSIGQ

MFETTMRGAKRMAILGDTAWDFGSLGGVFTSIGKALHQVFGAIYGAAFSG

VSWTMKILIGVIITWIGMNSRSTSLSVSLVLVGVVTLYLGVMVQA

DENV strain 3 envelope protein has the following sequence, identified as SEQ ID No. 4:

MRCVGVGNRDFVEGLSGATWVDVVLEHGGCVTTMAKNKPTLDIELQKTEA

TQLATLRKLCIEGKITNITTDSRCPTQGEAXLPEEQDQNYVCKHTYVDRG

WGNGCGLFGKGSLVTCAKFQCLEPIEGKVVQYENLKYTVIITVHTGDQHQ

VGNETQGVTAEITPQASTTEAILPEYGTLGLECSPRTGLDFNEMILLTMK

NKAWMVHRQWFFDLPLPWTSGATTETPTWNRKELLVTFKNAHAKKQEVVV

LGSQEGAMHTALTGATEIQNSGGTSIFAGHLKCRLKMDKLELKGMSYAMC

TNTFVLKKEVSETQHGTILIKVEYKGEDXPCKIPFSTEDGQKAHNGRLI

TANPVVTKKEEPVNIEAEPPFGESNIVIGIGDNALKINWYKKGSSIGKMF

EATARGARRMAILGDTAWDFGSVGGVLNSLGKMVHQIFGSAYTALFSGVS

WVMKIGIGVLLTWIGLNSKNTSMSFSCIAIGIITLYLGAVVQA

DENV strain 4 envelope protein has the following sequence, identified as SEQ ID No. 5:

MRCVGVGNRDFVEGVSGGAWVDLVLEHGGCVTTMAQGKPTLDFELTKTTA

KEVALLRTYCIEASISNITTATRCPTQGEPYLKEEQDQQYICRRDVVDRG

WGNGCGLFGKGGVVTCAKFSCSGKITGNLVQIENLEYTVVVTVHNGDTHA

VGNDTSNHGVTATITPRSPSVEVKLPDYGELTLDCEPRSGIDFNEMILMK

MKKKTWLVHKQWFLDLPLPWTAGADTSEVHWNYKERMVTFKVPHAKRQDV

TVLGSQEGAMHSALAGATEVDSGDGNHMFAGHLKCKVRMEKLRIKGMSYT

MCSGKFSIDKEMAETQHGTTVVKVKYEGAGAPCKVPIEIRDVNKEKVVGR

VISSTPLAENTNSVTNIELEPPFGDSYIVIGVGNSALTLHWFRKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA

FIG. 13 shows an alignment of the YFV 17D strain envelope protein of and all four strains of DENV envelope protein. As used in this invention a "corresponding amino acid" is defined as follows. FIG. 13 may be used to calculate which amino acids of the DENV envelope protein corresponds to the amino acid of the YFV envelope protein. For example, FIG. 13 shows that the first amino acid of YFV envelope protein, alanine, corresponds to the first amino acid of all four strains of DENV envelope protein, methionine. By way of a further example, FIG. 13 may also be used to calculate that the 160$^{th}$ amino acid of the YFV envelope protein, lysine, corresponds to the following amino acids of the four strains of DENV envelope protein:

| DENV strain | Amino acid position | Amino acid |
| --- | --- | --- |
| DENV1 | 163$^{rd}$ | Threonine |
| DENV2 | 163$^{rd}$ | Lysine |
| DENV3 | 161$^{st}$ | Glutamic Acid |
| DENV4 | 163$^{rd}$ | Threonine |

A similar amino acid alignment may be created by practitioners in the art with other *flavivirus* envelope proteins, for example with West Nile Virus, St. Louis encephalitis, Dengue Fever virus, Japanese encephalitis, and Kunjin virus envelope proteins. These amino acid alignments could be used to determine which amino acid of the *flavivirus* envelope protein corresponded to any of the four strains of DENV envelope protein.

Any or all of amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, 388-393 of YFV envelope protein, SEQ ID No. 1, may be substituted with the corresponding amino acid of the desired strain of DENV envelope (E) protein to create the chimeric protein of the invention. The substitution may be made according to methods known to practitioners in the art. For example, site directed mutagenesis of the envelope protein may be performed to create the chimeric protein. Briefly, this method makes use of a short mutant DNA primer that binds specifically to the region being changed, but contains one or a small number of specific base changes that will result in a coding change to substitute the new specifically desired amino acid. The bacterial plasmid with the E gene is replicated using PCR amplification to generate new full-length mutant DNA strands. Then the original DNA strand is degraded, leaving only the remaining specifically mutated DNA strand.

The chimeric protein is created by substituting amino acids of YFV envelope protein proximal to the domain II fusion loop. As used in this invention, amino acids "proximal to" the domain II fusion loop are those amino acids which are near the domain II fusion loop of the YFV envelope protein, shown in FIG. 13. In one embodiment, amino acids which are within 5 Å of the fusion loop are proximal to the fusion loop. In another embodiment, those amino acids which are within 14 Å of the fusion loop are proximal to the fusion loop are proximal to the fusion loop. Amino acids within 5 Å and 14 Å of the fusion loop are also shown in FIG. 13.

The fusion loop is a structural feature of *flavivirus* envelope proteins that is found on the tip of domain II and is responsible for direct interaction of the envelope (E) protein with the target cell lipid membrane. During the infection process, the fusion loop is projected outward by a structural rearrangement of the E protein, resulting in the fusion loop "harpooning" into the target cell membrane. This interaction is critical for the subsequent membrane fusion step, mediated by a further E protein movement that pulls the cell and virus membranes together. As shown in FIG. 13, the fusion loop is highly conserved in dengue and yellow fever viruses. The cysteine (C) at position 105 in the fusion loop forms a disulfide bond with the conserved cysteine (C) at position 74. This disulfide is important for the correct folding of the fusion loop. Amino acids within 5 Å and 14 Å of the fusion loop are important in YFV and DENV infection as well.

It is envisioned the chimeric protein may be used as a treatment composition for DENV infected individuals. It is further envisioned the chimeric protein may be used to create a treatment composition for preventing infection, or a vaccine effective against one or all four strains of DENV.

In an embodiment, the chimeric protein, such as for use in a vaccine, may use a small portion of the yellow fever virus (YFV) 17D vaccine strain envelope protein to be replaced by the corresponding portion from the dengue virus envelope protein. For an attenuated vaccine, the vaccine may use a replication competent YFV with the DENV/YFV hybrid E protein. An attenuated vaccine is created by reducing the virulence of a pathogen like YFV, but still keeping it viable (or "live"). Attenuation takes an infectious agent and alters it so that it becomes harmless or less virulent. These vaccines contrast to those produced by "killing" the virus (inactivated vaccine). Alternately, the invention could be used to develop a subunit vaccine that is not replicative. Rather than introducing an inactivated or attenuated microorganism to an immune system (which would constitute a "whole-agent" vaccine), a fragment of it can create an immune response, and relate to producing a subunit vaccine.

There is also presented by the invention methods for controlling a *flavivirus* entry into a cell, and methods of treating and preventing flaviviruses infections, together with vaccine and pharmaceutical compositions. Along with dengue, the family Flaviviridae contains at least 70 arthropod-transmitted viruses, many of which infect humans and other vertebrates. Subgroups of the Flaviviridae family include West Nile, Japanese Encephalitis, tick borne encephalitis, etc. the Japanese encephalitis serocomplex, includes West Nile Virus, St. Louis encephalitis, Murray Valley encephalitis, kunjin and other viruses. As an alternate approach to the use of a small portion of the yellow fever virus (YFV) 17D vaccine strain envelope protein to be replaced by the corresponding portion from the dengue virus envelope protein, the invention may swap out the dengue neutralizing epitopes into any other related *flavivirus*.

All flaviviruses, including West Nile Virus, St Louis encephalitis, dengue, Japanese encephalitis, yellow fever and kunjin viruses share similar size, symmetry and appearance. Despite the fact that flaviviruses may use different process to enter a host cell, such as endocytotis (described for West Nile Virus and Kunjin Virus) and direct fusion of the cell (described for dengue and Encephalitis Virus), entry of all flaviviruses into the host-cell involves an interaction between the virus and a receptor of the cell.

As the viral envelope protein of flaviviruses plays a role in mediating virus-host cellular receptor interaction, the invention contemplates use of dengue neutralizing epitopes into any other related *flavivirus*.

The invention creates a vaccine that will induce broadly protective antibodies against dengue virus and reduce the induction of non-neutralizing antibodies that will cause enhancement. The invention relates to a vaccine and methods of producing a vaccine using information from defining the regions of the E protein that are responsible for inducing a neutralizing antibody response to dengue. Neutralizing antibodies can produce the infection enhancing effect, but they only do so at sub-neutralizing concentrations, while non-neutralizing antibodies produce enhancement at all concentrations. The invention recognizes that if the human antibody response could be shifted away from a non-neutralizing response and towards a neutralizing response, this could considerably reduce the risk of post-vaccination disease enhancement. The invention provides a vaccine that substantially reduces the risk of inducing an enhancing antibody response. A vaccine formulation could accomplish this by only including the dengue E protein epitopes that induce a neutralizing response, and not including the epitopes that produce a non-neutralizing response. The invention describes a common class of human, broadly neutralizing monoclonal antibodies and identifies their binding epitope, allowing the design a vaccine formulation. The invention has confirmed the envelope portion from dengue virus that will be replaced in the yellow fever vaccine strain, and contemplates using common techniques to allow the resulting chimeric viruses to grow well enough to provide a suitable vaccine response.

The broadly neutralizing monoclonal antibodies were determined from each of three dengue patients infected in Jamaica, Singapore, and Myanmar, at time points two weeks, two months, and two years post infection. These antibodies (4.8A, D11Ckl, and 1.6D) show neutralization activity against all four serotypes of dengue and recognize a common epitope consisting of the E protein fusion loop and nearby regions. They target this region because they interfere with the binding of a previously characterized mouse monoclonal antibody that is known to target the fusion loop (4G2) and they interfere with each other's binding.

Confirmation of the fusion loop as a target comes from mechanistic experiments. These antibodies do not interfere with virus: cell binding, but do inhibit the ability of virus to fuse with liposomes. There is further defined their epitopes through binding experiments with a large panel of E protein mutants. Mutations in the E protein that prevent binding of these antibodies map to locations in and near to the fusion loop.

These antibodies (4.8A, D11Ckl, and 1.6D) do not show strong neutralization activity against yellow fever virus, indicating that the yellow fever virus E protein lacks the important amino acid sequences that are recognized by these antibodies. Because the fusion loops of dengue and yellow fever are identical, the important amino acid positions lie outside of the fusion loop. An amino acid sequence alignment of the dengue and yellow fever E proteins shows the differences between dengue and yellow fever that are responsible for antibody recognition.

Exchange of these dengue specific amino acid sequences into the yellow fever E protein will yield a chimeric E protein that will induce and be recognized by neutralizing antibodies against dengue. This chimeric E protein can be used as a modification to the yellow fever 17-D vaccine, one of the most successful vaccines ever developed.

Figure 1B:
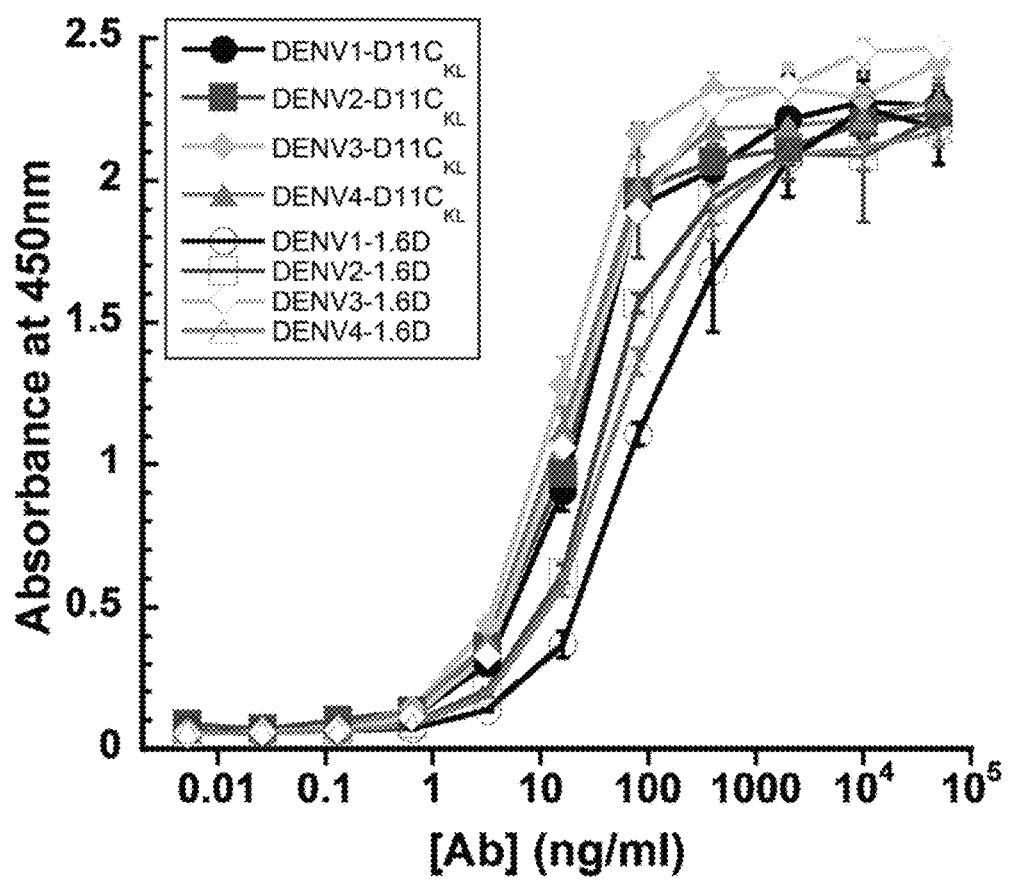
FIG. 1B shows the results of ELISA assays with immobilized virus envelope glycoproteins, patient sera, and monoclonal antibodies from DENV infected patients at different antibody concentrations.

FIGS. 1A and 1B establishes DENV specificity and broad reactivity of patient sera.

Figure 2:
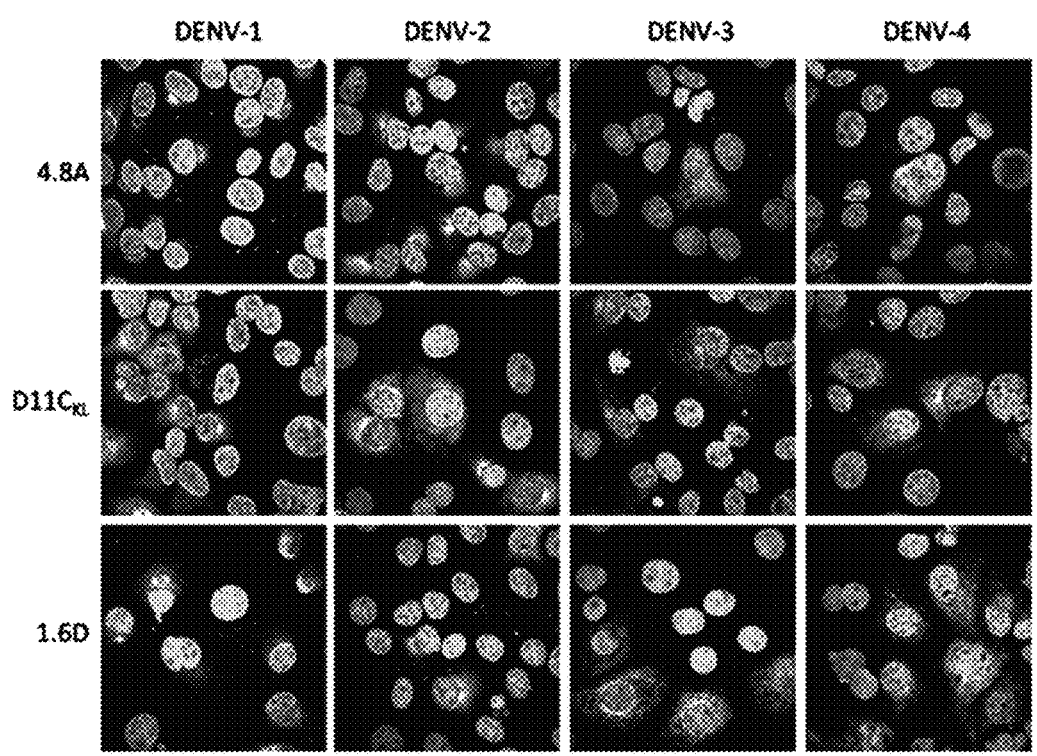
FIG. 2 shows the results of immunofluorescence assays with DENV-1 to 4 infected LLC-MK-2 cells exposed to monoclonal antibodies from DENV infected patients.
Figure 3A:
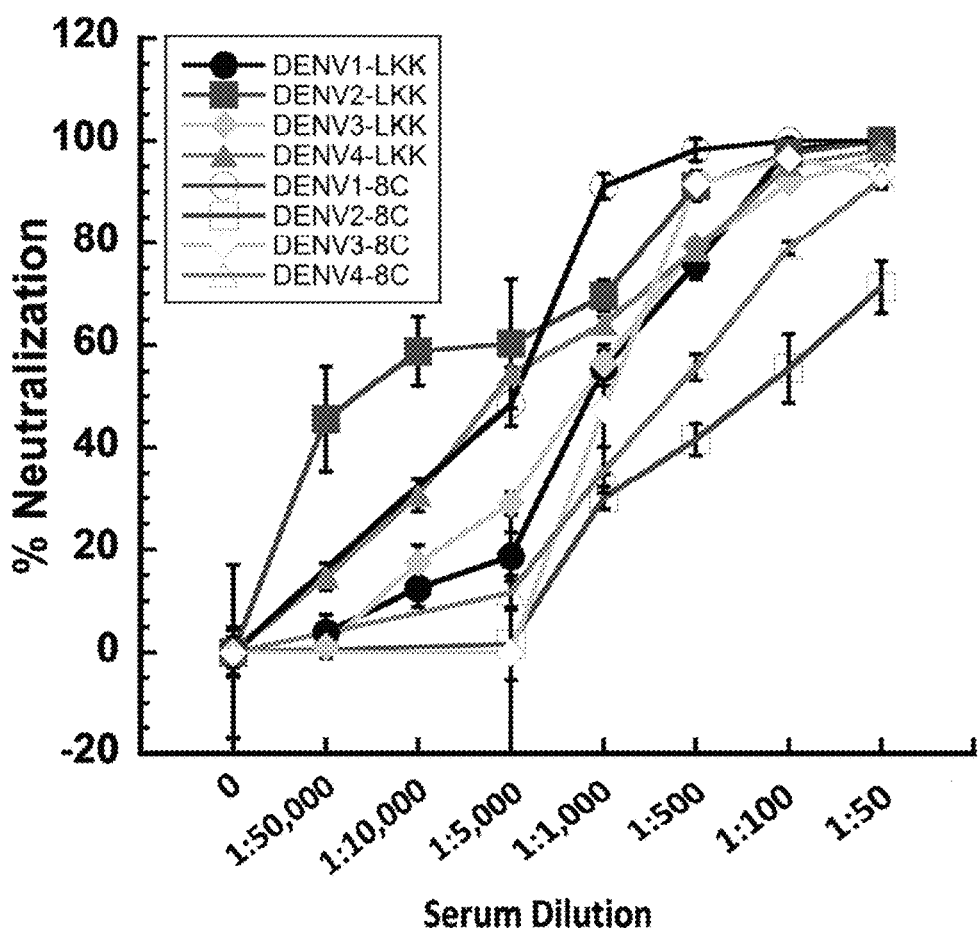
FIG. 3A shows the results of neutralization assays with DENV-1 to 4 infected LLC-MK-2 cells using patient sera from DENV infected patients.
Figure 3B:
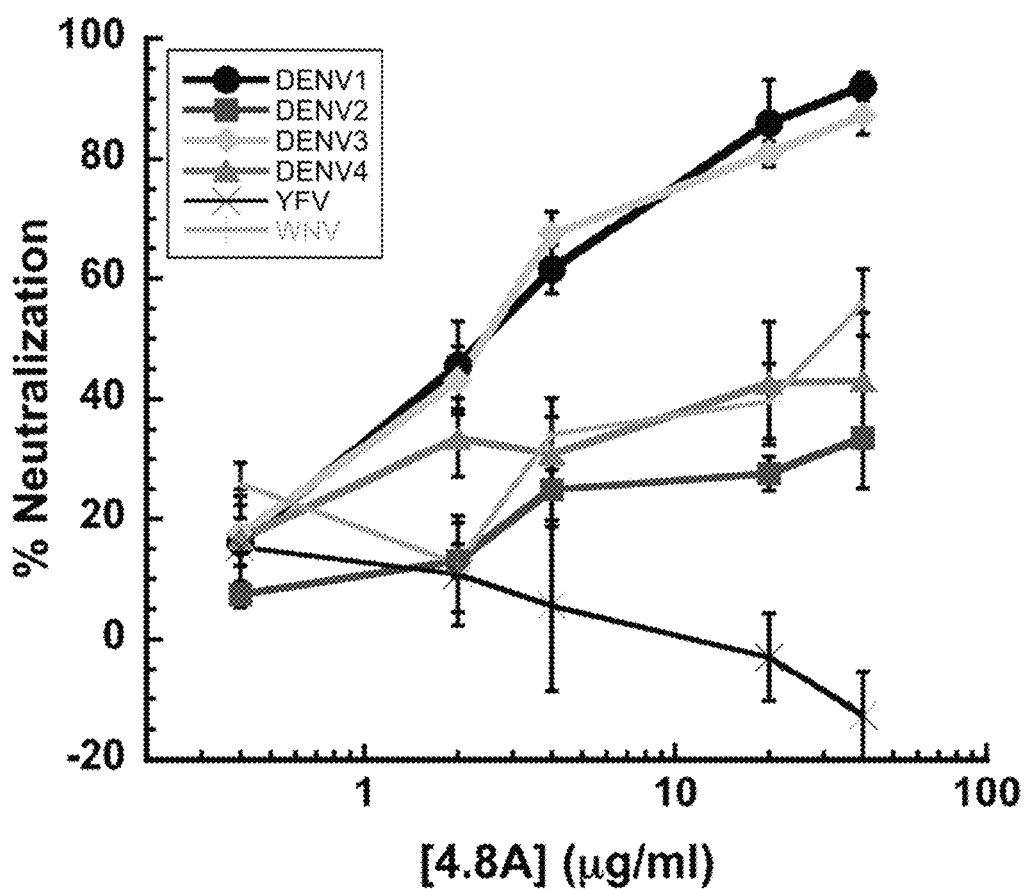
FIG. 3B shows the results of neutralization assays with DENV-1 to 4 infected LLC-MK-2 cells, using monoclonal antibody 4.8A from DENV infected patients.
Figure 3C:
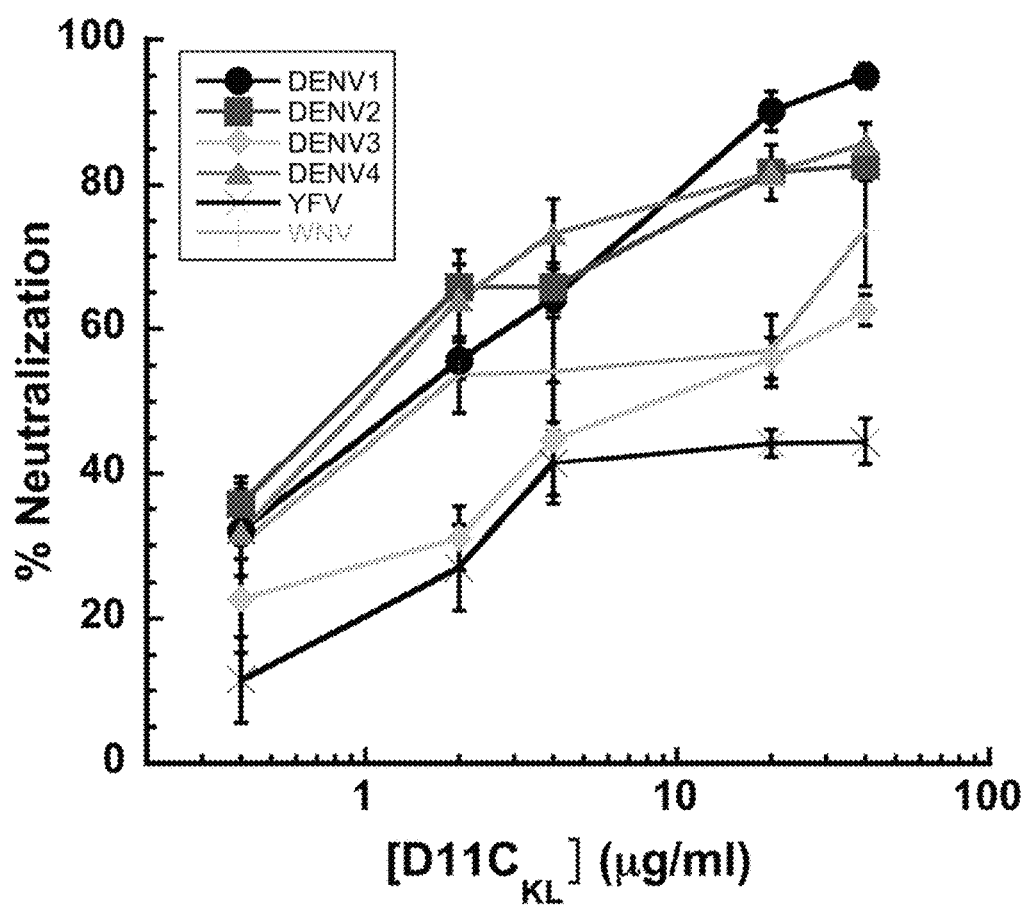
FIG. 3C shows the results of neutralization assays with DENV-1 to 4 infected LLC-MK-2 cells, using monoclonal antibody $D11C_{KL}$ from DENV infected patients.
Figure 3D:
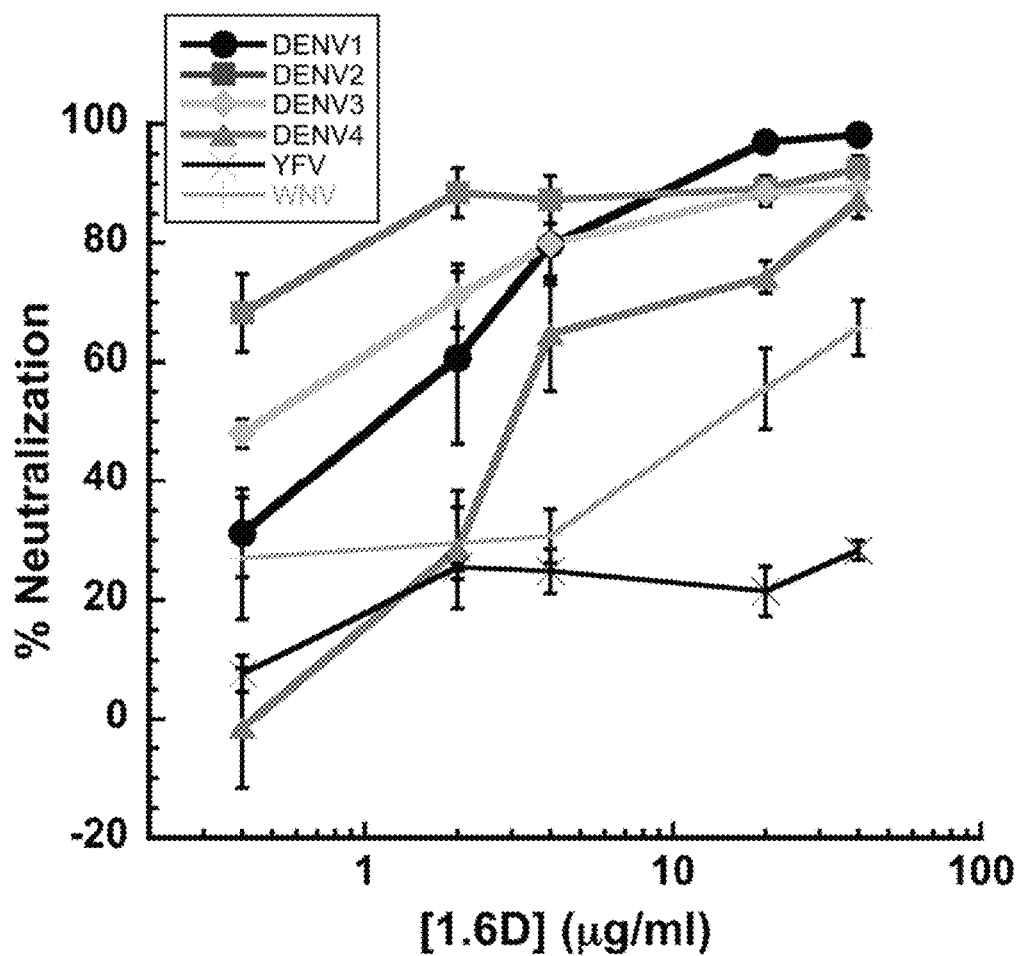
FIG. 3D shows the results of neutralization assays with DENV-1 to 4 infected LLC-MK-2 cells, using monoclonal antibody 1.6D from DENV infected patients.
Figure 4A:
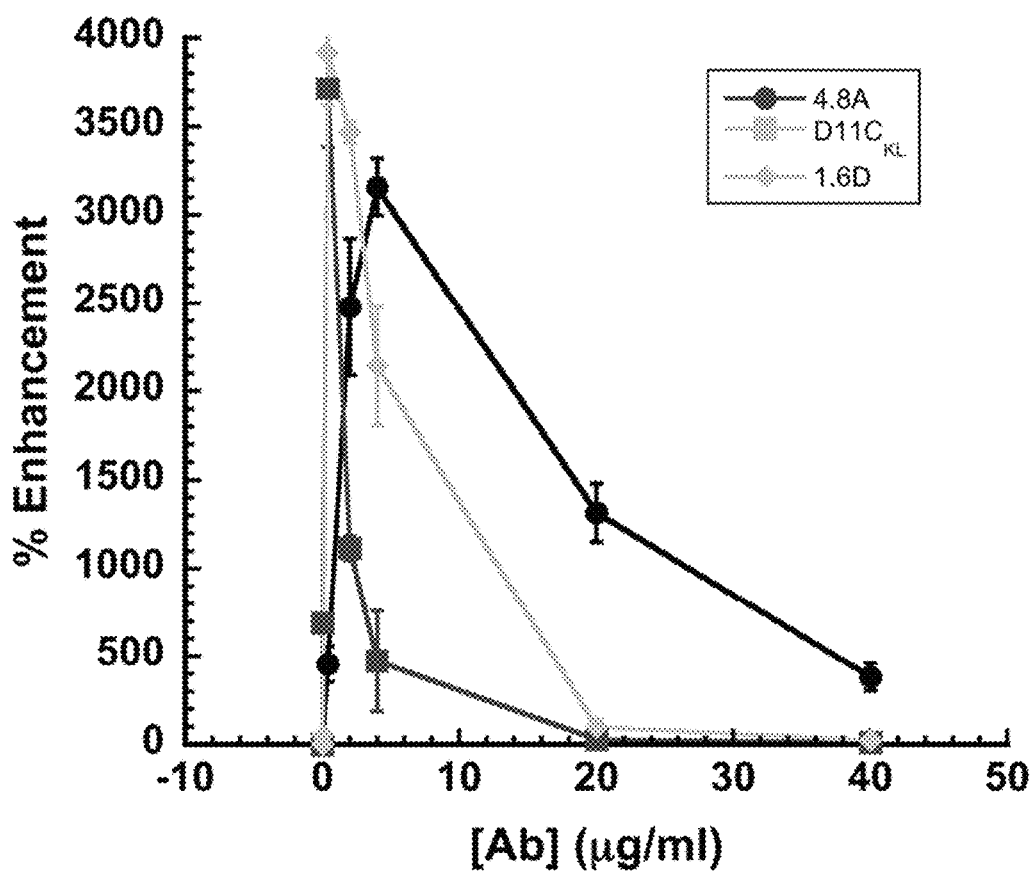
FIG. 4A shows the viral uptake results from enhancement assays performed in the presence of monoclonal antibodies from DENV infected patients.
Figure 4B:
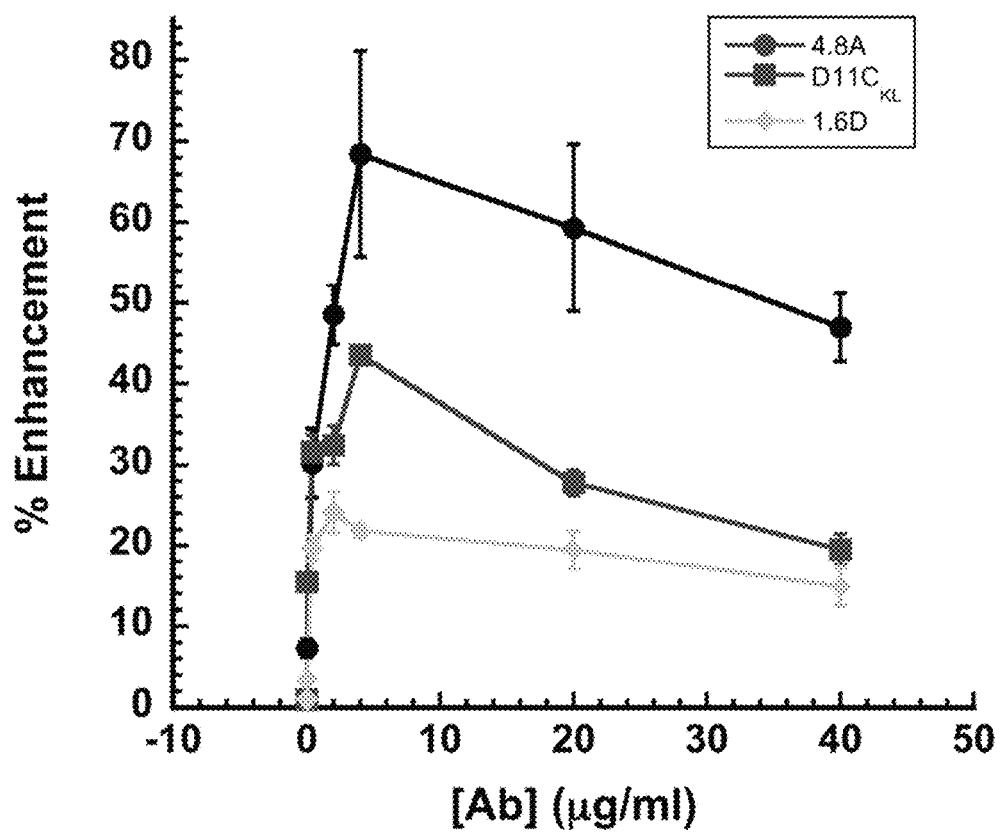
FIG. 4B shows the viral uptake results from enhancement assays performed in the presence of monoclonal antibodies from DENV infected patients.
Figure 4C:
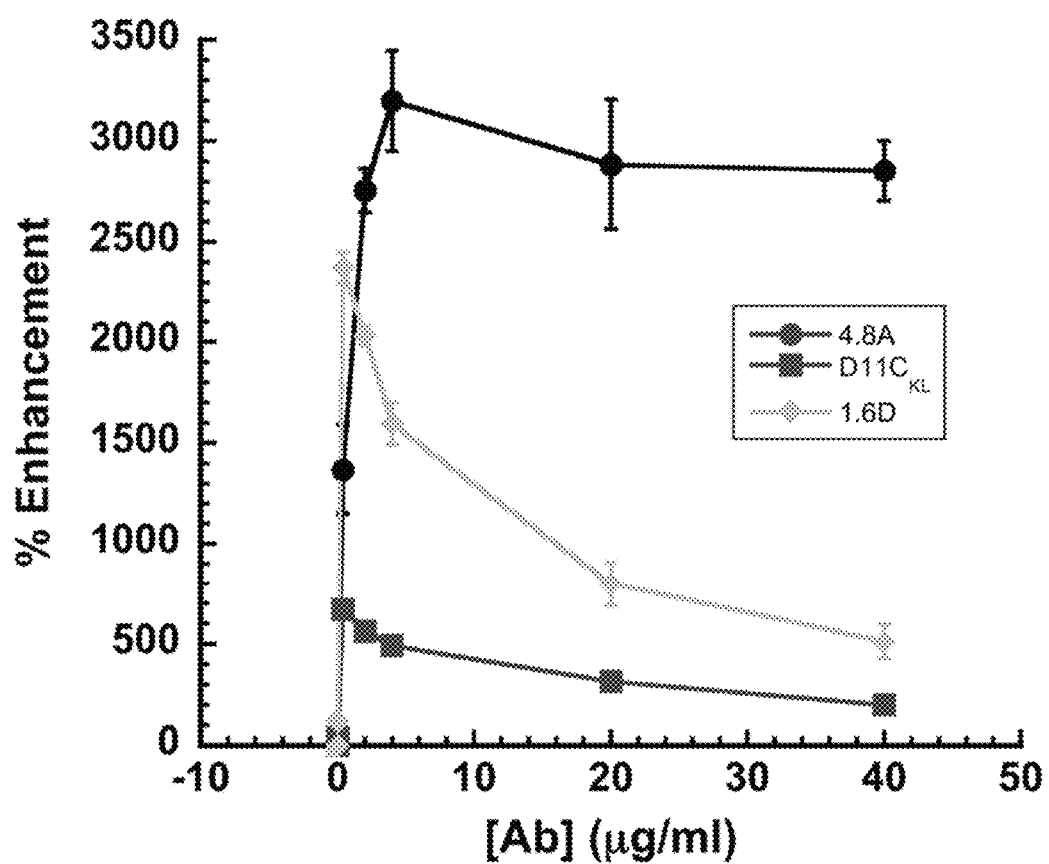
FIG. 4C shows the viral uptake results from enhancement assays performed in the presence of monoclonal antibodies from DENV infected patients.
Figure 4D:
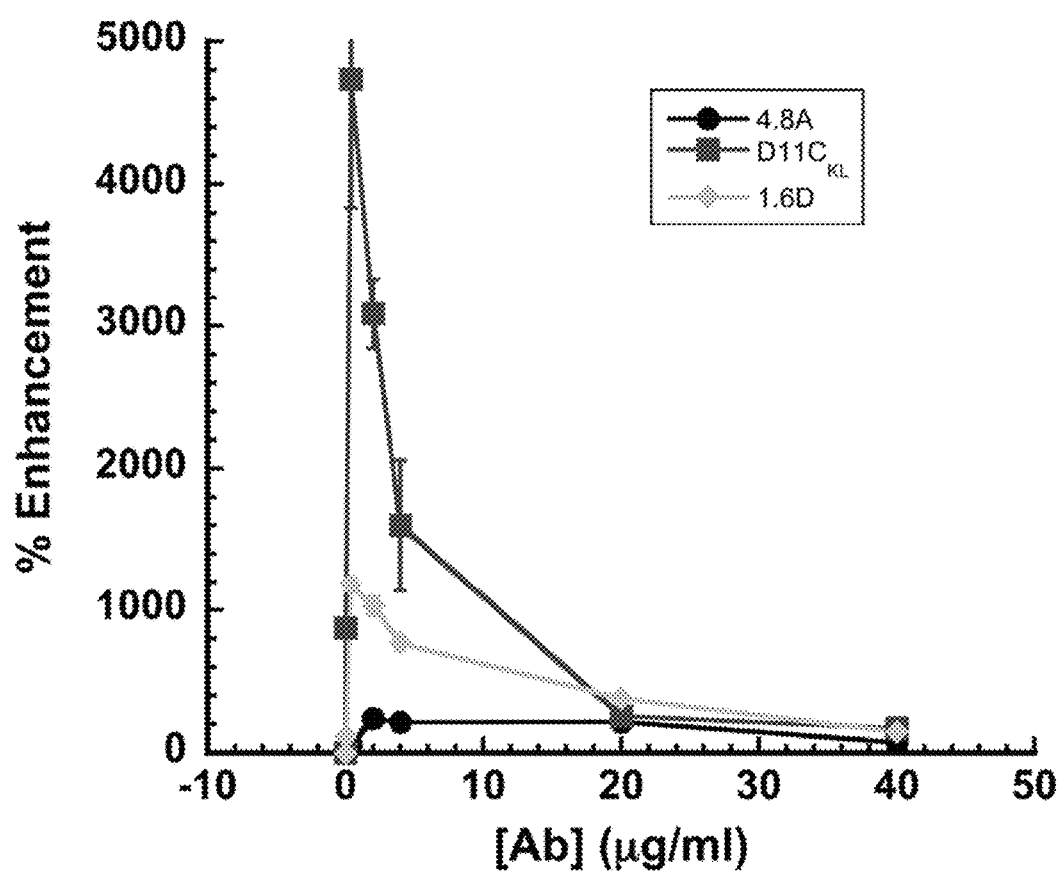
FIG. 4D shows the viral uptake results from enhancement assays performed in the presence of monoclonal antibodies from DENV infected patients.

FIG. 2 establishes specificity for DENV antigens in the context of a cell.

FIGS. 3A through 3D establishes neutralization activity of patient sera and of monoclonal antibodies from DENV infected patients.

FIGS. 4A through 4D establishes that enhancing concentrations correlate with binding affinity to DENV-1 to 4, and also shows neutralization.

Figure 5:
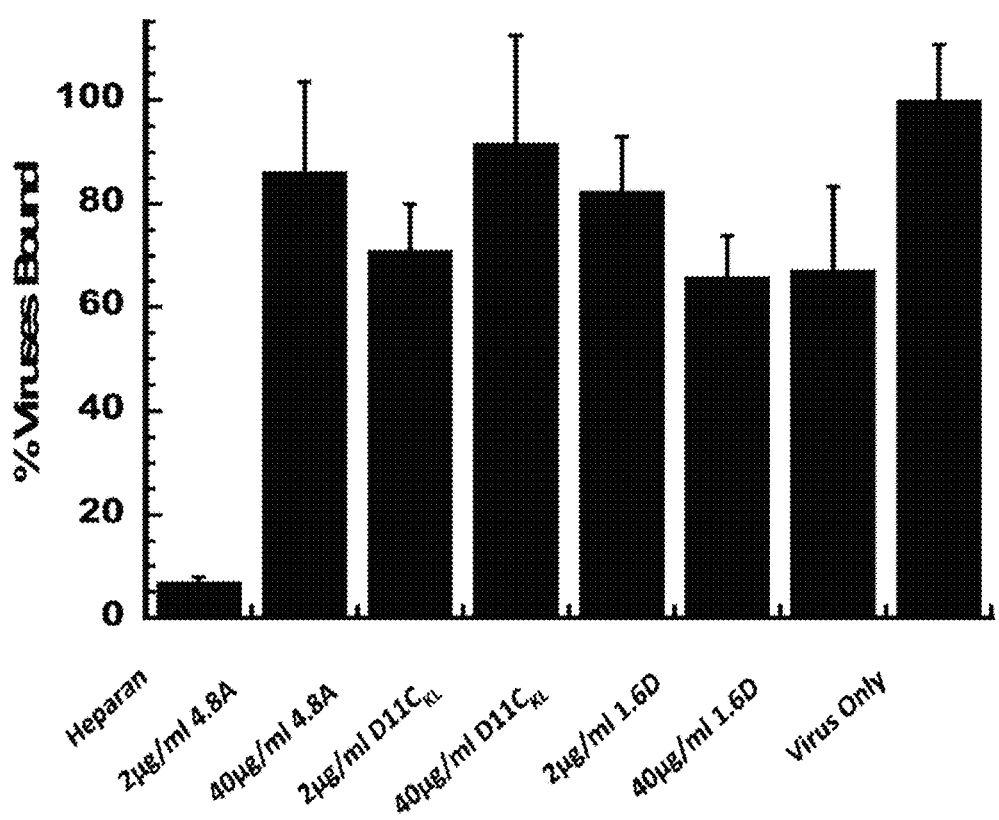
FIG. 5 shows the results from virus-cell binding inhibition assays performed in the presence of monoclonal antibodies from DENV infected patients.

FIG. 5 rules out binding inhibition as mechanism.

Figure 6:
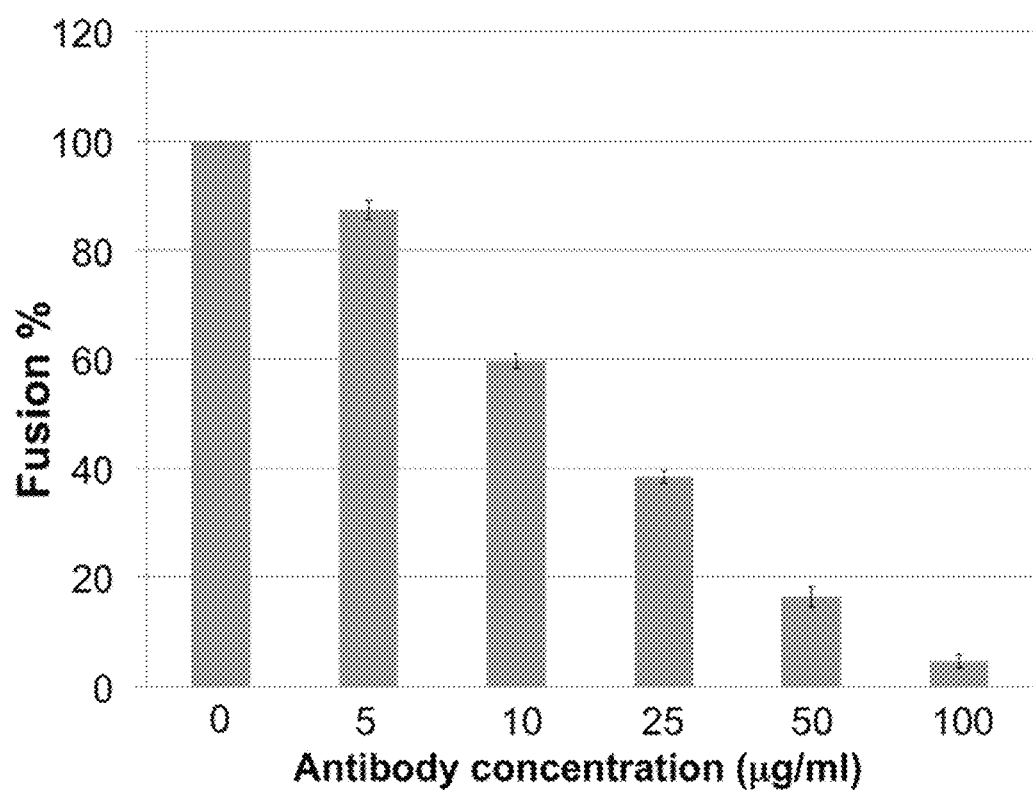
FIG. 6 shows the results from virus-liposome binding inhibition assays performed in the presence of monoclonal antibodies from DENV infected patients.

FIG. 6 establishes mechanism as fusion inhibition for monoclonal antibody D11Ckl.

Figure 7:
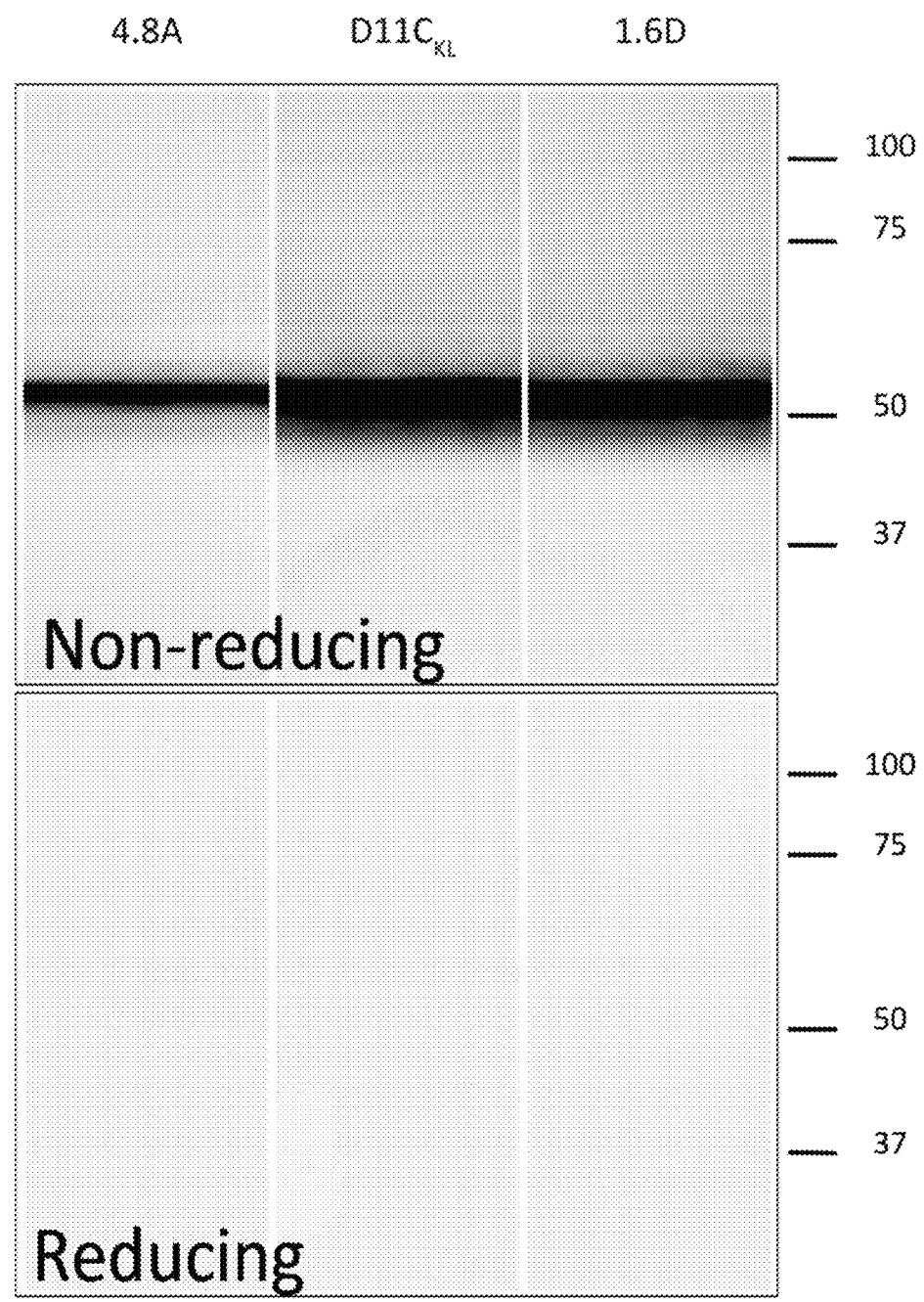
FIG. 7 shows the results from Western blot assays performed with purified DENV-2 and probed with monoclonal antibodies from DENV infected patients.

FIG. 7 shows that the monoclonal antibodies from DENV infected patients bind to protein consistent with size of E and the epitope is conformationally sensitive.

Figures 8, 9:
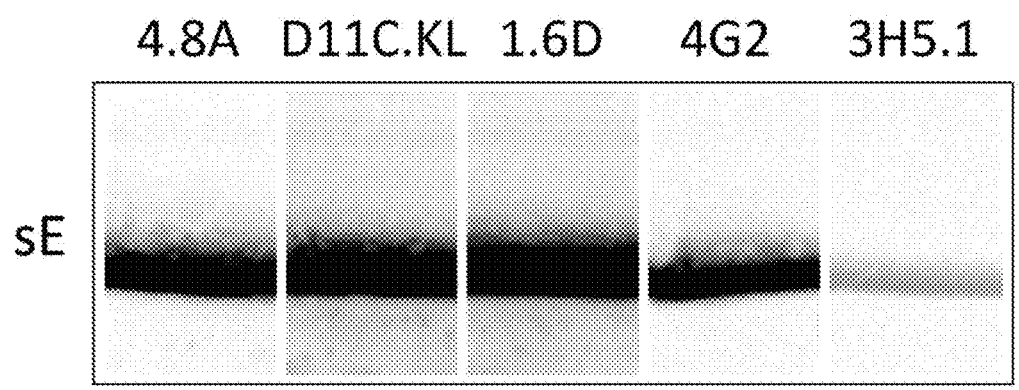
FIG. 8 shows the results from Western blot assays performed with soluble protein E and probed with monoclonal antibodies from DENV infected patients.
FIG. 9 shows the results from epitope mapping and gives the dissociation constants of monoclonal antibodies from DENV infected patients to soluble protein E.

FIG. 8 confirms that the monoclonal antibodies from DENV infected patients bind to E, specifically to the ectodomain.

FIG. 9 determines how tightly the monoclonal antibodies from DENV infected patients bind to E protein.

Figure 10:
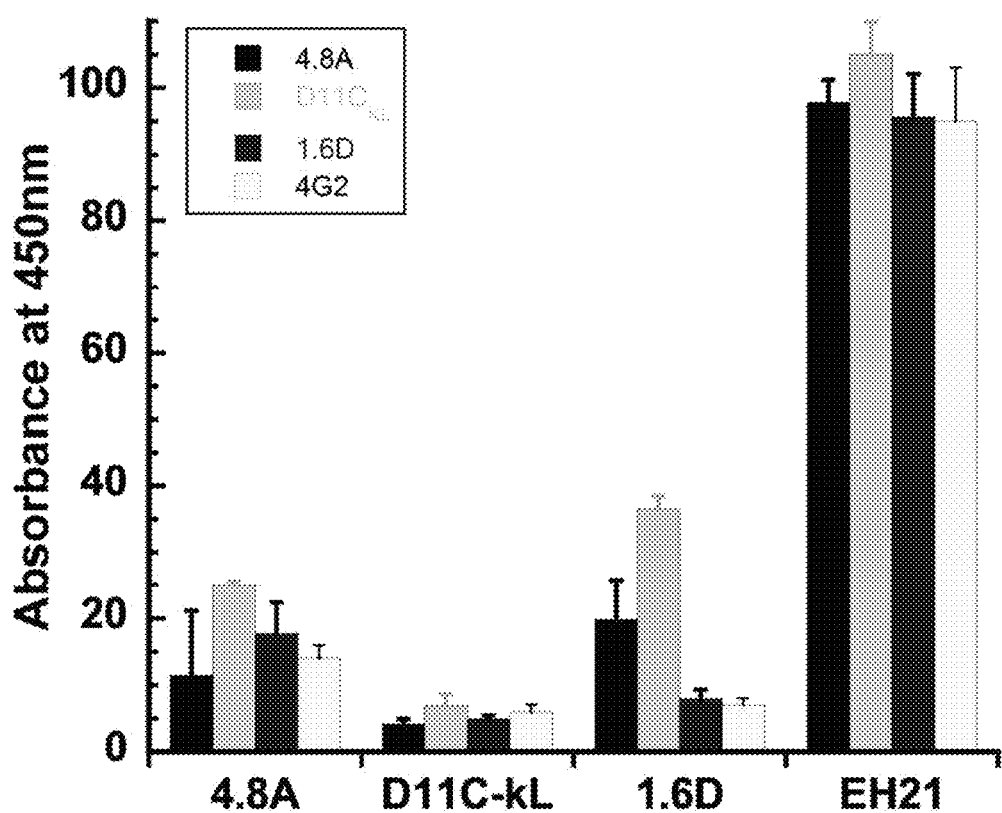
FIG. 10 shows the results from binding competition ELISA assays with monoclonal antibodies from DENV infected patients and 4G2.

FIG. 10 establishes that monoclonal antibodies from DENV infected patients compete for same domain as 4G2, a known fusion loop binder.

Figure 11:
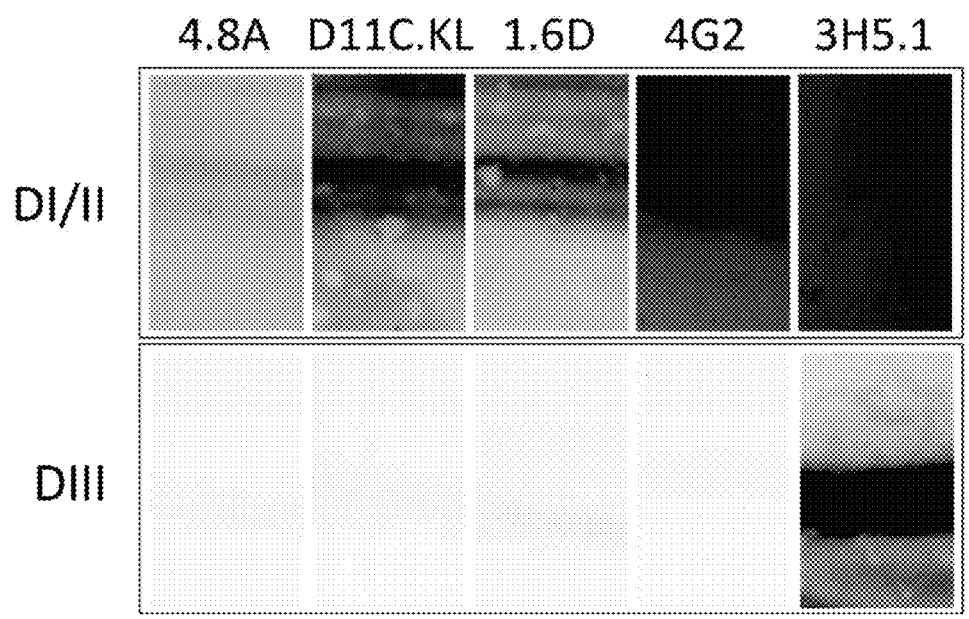
FIG. 11 shows the results from Western blot assays performed with DI/II and DIII and probed with monoclonal antibodies from DENV infected patients.

FIG. 11 establishes that monoclonal antibodies from DENV infected patients bind to DI/II consistent with fusion inhibition and competition assays.

Figure 12:
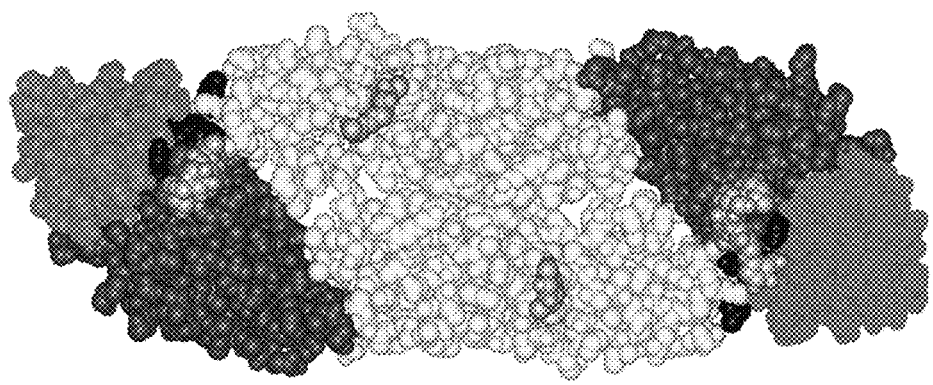
FIG. 12 shows the residues for monoclonal antibodies from DENV infected patients mapped to E protein crystal structure.

FIG. 12 confirms monoclonal antibody 4.8A epitope as fusion loop and/or vicinity.

FIG. 13 highlights the amino acids in yellow fever virus 17-D envelope protein which may be substituted with the DENV-1 to 4 envelope amino acids to create a chimeric E protein. It highlights the desirable amino acid substitution locations, as well as proposed amino acid substitutions.

Figure 14:
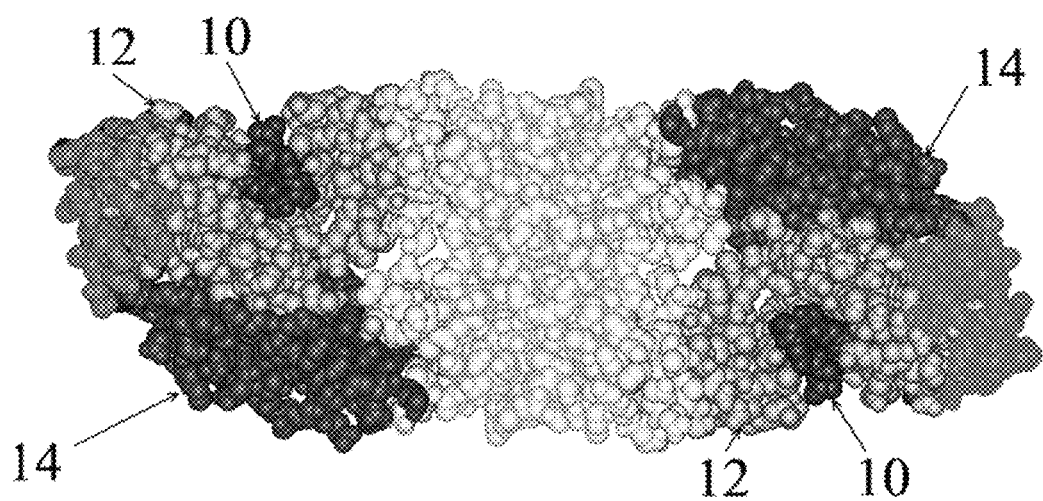
FIG. 14 shows the protein crystal structure of the DENV envelope protein and demonstrates the location of the fusion loop (black) and 5 Å (green) and 14 Å (teal) surrounding amino acids.

FIG. 14 shows the protein crystal structure of the DENV envelope protein and demonstrates the location of the fusion loop at 10 and 5 Å at 12 and 14 Å at 14 surrounding amino acids.

In still another aspect, the invention includes a vaccine for immunizing an individual against dengue hemorrhagic fever and/or dengue shock syndrome. The vaccine includes one or more peptides of the type described, in a pharmaceutically acceptable adjuvant.

It should be recognized that the invention provides a dengue vaccine and methods using a small portion of the yellow fever virus 17D vaccine strain envelope protein (or other related faviviruses) to be replaced by the corresponding portion from the dengue virus envelope protein. This creates a chimeric protein, such as for use in a vaccine, that will induce broadly protective antibodies against dengue virus and reduce the induction of non-neutralizing antibodies that will cause enhancement. While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to any particular embodiment disclosed, but that the invention will include all embodiments falling within the scope of the appended claims.

What is claimed is:

1. A chimeric protein, comprising:
an envelope protein comprised of yellow fever virus 17-D envelope protein having SEQ ID No: 1;
wherein selected amino acids of the yellow fever virus 17-D envelope protein are substituted with corresponding amino acids of dengue fever virus envelope protein selected from the group consisting of SEQ ID No: 2, SEQ ID No: 3, SEQ ID No: 4, and SEQ ID No: 5;
wherein one or more of amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, and 388-393 of SEQ ID No: 1 are substituted with the corresponding amino acids of the selected dengue fever virus envelope protein.

2. The chimeric protein of claim 1, wherein the substituted amino acids comprise the amino acids proximal to a Domain II fusion loop.

3. The chimeric protein of claim 2, wherein the substituted amino acids comprise the amino acids within 5 Å of the fusion loop.

4. The chimeric protein of claim 2, wherein the substituted amino acids comprise the amino acids within 14 Å of the fusion loop.

5. A method of treating a dengue fever virus infection, the method comprising the step of administering the chimeric protein of claim 1.

6. A composition for treatment of dengue fever virus, comprising:
a chimeric envelope protein comprised of a flavivirus envelope protein, wherein selected amino acids of the flavivirus envelope protein are substituted with corresponding amino acids of dengue fever virus envelope protein selected from the group consisting of SEQ ID No: 2, SEQ ID No: 3, SEQ ID No: 4, and SEQ ID No: 5; and
a pharmaceutically acceptable excipient;
wherein one or more of amino acids 1-11, 28-30, 32, 42, 44, 46, 70-81, 95-99, 110-115, 142-147, 149-157, 236-242, 304-324, 333, 335, 337, 350-352, 355, 356, 362-370, 377, 379, 386, and 388-393 of SEQ ID No: 1 are substituted with the corresponding amino acids of the selected dengue fever virus envelope protein.

7. The composition of claim 6, wherein the flavivirus is selected from the group consisting of West Nile Virus, St. Louis encephalitis, Dengue Fever virus, Japanese encephalitis, Yellow Fever virus, and Kunjin virus.

8. The composition of claim 6, wherein the substituted amino acids comprise the amino acids proximal to a fusion loop.

9. The composition of claim 8, wherein the substituted amino acids comprise the amino acids within 5 Å of the fusion loop.

10. The composition of claim 8, wherein the substituted amino acids comprise the amino acids within 14 Å of the fusion loop.

11. A method of treating a dengue fever virus infection, the method comprising the step of administering the composition of claim 6.

12. The chimeric protein of claim 1, wherein the amino acids 70-73, 76-77, 97, 113and 115 of SEQ ID NO:1 are substituted with the corresponding amino acids in SEQ ID NO:4.

13. The composition for treatment of dengue fever virus of claim 6, wherein the amino acids 70-73, 76-77, 97, 113 and 115 of SEQ ID NO:1 are substituted with the corresponding amino acids in SEQ ID NO:4.

* * * * *

UNITED STATES PATENT AND TRADEMARK OFFICE
CERTIFICATE OF CORRECTION

PATENT NO. : 10,124,053 B2
APPLICATION NO. : 15/413347
DATED : November 13, 2018
INVENTOR(S) : Isern et al.

Page 1 of 1

It is certified that error appears in the above-identified patent and that said Letters Patent is hereby corrected as shown below:

In the Specification

On Column 17, Line 19, (approx.) after the "GOVERNMENT SUPPORT" section, please insert the following passage after the recitation of the government agency "Defense Threat Reduction Agency":
-- and grant no. R01AI099210 awarded by the National Institute of Allergy and Infectious Diseases --

Signed and Sealed this
Fourth Day of June, 2019

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 493
<212> TYPE: PRT
<213> ORGANISM: Flavivirus yellow fever virus

<400> SEQUENCE: 1

Ala His Cys Ile Gly Ile Thr Asp Arg Asp Phe Ile Glu Gly Val His
1               5                   10                  15

Gly Gly Thr Trp Val Ser Ala Thr Leu Glu Gln Asp Lys Cys Val Thr
            20                  25                  30

Val Met Ala Pro Asp Lys Pro Ser Leu Asp Ile Ser Leu Glu Thr Val
        35                  40                  45

Ala Ile Asp Arg Pro Ala Glu Val Arg Lys Val Cys Tyr Asn Ala Val
    50                  55                  60

Leu Thr His Val Lys Ile Asn Asp Lys Cys Pro Ser Thr Gly Glu Ala
65                  70                  75                  80

His Leu Ala Glu Glu Asn Glu Gly Asp Asn Ala Cys Lys Arg Thr Tyr
                85                  90                  95

Ser Asp Arg Gly Trp Gly Asn Gly Cys Gly Leu Phe Gly Lys Gly Ser
            100                 105                 110

Ile Val Ala Cys Ala Lys Phe Thr Cys Ala Lys Ser Met Ser Leu Phe
        115                 120                 125
```

-continued

Glu Val Asp Gln Thr Lys Ile Gln Tyr Val Ile Arg Ala Gln Leu His
            130                 135                 140

Val Gly Ala Lys Gln Glu Asn Trp Asn Thr Asp Ile Lys Thr Leu Lys
145                 150                 155                 160

Phe Asp Ala Leu Ser Gly Ser Gln Glu Val Glu Phe Ile Gly Tyr Gly
                165                 170                 175

Lys Ala Thr Leu Glu Cys Gln Val Gln Thr Ala Val Asp Phe Gly Asn
            180                 185                 190

Ser Tyr Ile Ala Glu Met Glu Thr Glu Ser Trp Ile Val Asp Arg Gln
            195                 200                 205

Trp Ala Gln Asp Leu Thr Leu Pro Trp Gln Ser Gly Ser Gly Gly Val
210                 215                 220

Trp Arg Glu Met His His Leu Val Glu Phe Glu Pro Pro His Ala Ala
225                 230                 235                 240

Thr Ile Arg Val Leu Ala Leu Gly Asn Gln Glu Gly Ser Leu Lys Thr
                245                 250                 255

Ala Leu Thr Gly Ala Met Arg Val Thr Lys Asp Thr Asn Asp Asn Asn
            260                 265                 270

Leu Tyr Lys Leu His Gly Gly His Val Ser Cys Arg Val Lys Leu Ser
            275                 280                 285

Ala Leu Thr Leu Lys Gly Thr Ser Tyr Lys Ile Cys Thr Asp Lys Met
290                 295                 300

Phe Phe Val Lys Asn Pro Thr Asp Thr Gly His Gly Thr Val Val Met
305                 310                 315                 320

Gln Val Lys Val Ser Lys Gly Ala Pro Cys Arg Ile Pro Val Ile Val
                325                 330                 335

Ala Asp Asp Leu Thr Ala Ala Ile Asn Lys Gly Ile Leu Val Thr Val
            340                 345                 350

Asn Pro Ile Ala Ser Thr Asn Asp Asp Glu Val Leu Ile Glu Val Asn
            355                 360                 365

Pro Pro Phe Gly Asp Ser Tyr Ile Ile Val Gly Arg Gly Asp Ser Arg
            370                 375                 380

Leu Thr Tyr Gln Trp His Lys Glu Gly Ser Ser Ile Gly Lys Leu Phe
385                 390                 395                 400

Thr Gln Thr Met Lys Gly Val Glu Arg Leu Ala Val Met Gly Asp Thr
                405                 410                 415

Ala Trp Asp Phe Ser Ser Ala Gly Gly Phe Phe Thr Ser Val Gly Lys
            420                 425                 430

Gly Ile His Thr Val Phe Gly Ser Ala Phe Gln Gly Leu Phe Gly Gly
            435                 440                 445

Leu Asn Trp Ile Thr Lys Val Ile Met Gly Ala Val Leu Ile Trp Val
450                 455                 460

Gly Ile Asn Thr Arg Asn Met Thr Met Ser Met Ser Met Ile Leu Val
465                 470                 475                 480

Gly Val Ile Met Met Phe Leu Ser Leu Gly Val Gly Ala
                485                 490

<210> SEQ ID NO 2
<211> LENGTH: 495
<212> TYPE: PRT
<213> ORGANISM: Flavivirus dengue virus
<220> FEATURE:
<221> NAME/KEY: misc_feature
<222> LOCATION: (171)..(171)
<223> OTHER INFORMATION: Xaa can be any naturally occurring amino acid

<400> SEQUENCE: 2

```
Met Arg Cys Val Gly Ile Gly Ser Arg Asp Phe Val Glu Gly Leu Ser
1               5                   10                  15

Gly Ala Thr Trp Val Asp Val Leu Glu His Gly Ser Cys Val Trp
            20                  25                  30

Thr Met Ala Lys Asp Lys Pro Thr Leu Asp Ile Glu Leu Leu Lys Thr
            35                  40                  45

Glu Val Thr Asn Pro Ala Val Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
            115                 120                 125

Ile Val Gln Tyr Glu Asn Leu Lys Tyr Ser Val Ile Thr Val His
            130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Xaa Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Gln Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Ile Lys Tyr Glu Gly Thr Asp Ala Pro Cys Lys Ile Pro
                325                 330                 335

Phe Ser Thr Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Ile Gly Ala Gly Glu
    370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415
```

-continued

```
Asp Thr Ala Trp Asp Phe Gly Ser Ile Gly Gly Val Phe Thr Ser Val
            420                 425                 430

Gly Lys Leu Val His Gln Ile Phe Gly Thr Ala Tyr Gly Val Leu Phe
            435                 440                 445

Ser Gly Val Ser Trp Thr Met Lys Ile Gly Ile Gly Val Leu Leu Thr
450                 455                 460

Trp Leu Gly Leu Asn Ser Arg Ser Thr Ser Leu Ser Met Thr Cys Ile
465                 470                 475                 480

Ala Val Gly Leu Val Thr Leu Tyr Leu Gly Val Met Val Gln Ala
                485                 490                 495

<210> SEQ ID NO 3
<211> LENGTH: 494
<212> TYPE: PRT
<213> ORGANISM: Flavivirus dengue virus
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid

<400> SEQUENCE: 3

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Xaa Val Gln Pro Glu Asn Leu Glu Tyr Thr Ile Val Ile Thr Pro His
130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Glu Met Val Leu Leu Gln Met Glu Xaa Lys Ala Trp Leu Val His
        195                 200                 205

Arg Gln Trp Phe Leu Asp Leu Pro Leu Pro Trp Leu Pro Gly Ala Asp
    210                 215                 220

Thr Gln Gly Ser Asn Trp Ile Gln Lys Glu Thr Leu Val Thr Phe Lys
```

```
                    225                 230                 235                 240
        Asn Pro His Ala Lys Lys Gln Asp Val Val Leu Gly Ser Gln Glu
                        245                 250                 255
        Gly Ala Met His Thr Ala Leu Thr Gly Ala Thr Glu Ile Gln Met Ser
                        260                 265                 270
        Ser Gly Asn Leu Leu Phe Thr Gly His Leu Lys Cys Arg Leu Arg Met
                        275                 280                 285
        Asp Lys Leu Gln Leu Lys Gly Met Ser Tyr Ser Met Cys Thr Gly Lys
                        290                 295                 300
        Phe Lys Xaa Val Lys Glu Ile Ala Glu Thr Gln His Gly Thr Ile Val
        305                 310                 315                 320
        Ile Arg Val Gln Tyr Glu Gly Asp Gly Ser Pro Cys Lys Ile Pro Phe
                        325                 330                 335
        Glu Ile Met Asp Leu Glu Lys Arg His Val Leu Gly Arg Leu Ile Thr
                        340                 345                 350
        Val Asn Pro Ile Val Thr Glu Lys Asp Ser Pro Val Asn Ile Glu Ala
                        355                 360                 365
        Glu Pro Pro Phe Gly Asp Ser Tyr Ile Ile Ile Gly Val Glu Pro Gly
                        370                 375                 380
        Gln Leu Lys Leu Asn Trp Phe Lys Lys Gly Ser Ser Ile Gly Gln Met
        385                 390                 395                 400
        Phe Glu Thr Thr Met Arg Gly Ala Lys Arg Met Ala Ile Leu Gly Asp
                        405                 410                 415
        Thr Ala Trp Asp Phe Gly Ser Leu Gly Gly Val Phe Thr Ser Ile Gly
                        420                 425                 430
        Lys Ala Leu His Gln Val Phe Gly Ala Ile Tyr Gly Ala Ala Phe Ser
                        435                 440                 445
        Gly Val Ser Trp Thr Met Lys Ile Leu Ile Gly Val Ile Ile Thr Trp
                        450                 455                 460
        Ile Gly Met Asn Ser Arg Ser Thr Ser Leu Ser Val Ser Leu Val Leu
        465                 470                 475                 480
        Val Gly Val Val Thr Leu Tyr Leu Gly Val Met Val Gln Ala
                        485                 490

<210> SEQ ID NO 4
<211> LENGTH: 493
<212> TYPE: PRT
<213> ORGANISM: Flavivirus dengue virus
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid

<400> SEQUENCE: 4

Met Arg Cys Val Gly Val Gly Asn Arg Asp Phe Val Glu Gly Leu Ser
        1               5                   10                  15
        Gly Ala Thr Trp Val Asp Val Val Leu Glu His Gly Gly Cys Val Thr
                        20                  25                  30
        Thr Met Ala Lys Asn Lys Pro Thr Leu Asp Ile Glu Leu Gln Lys Thr
                        35                  40                  45
        Glu Ala Thr Gln Leu Ala Thr Leu Arg Lys Leu Cys Ile Glu Gly Lys
                        50                  55                  60
        Ile Thr Asn Ile Thr Thr Asp Ser Arg Cys Pro Thr Gln Gly Glu Ala
```

-continued

```
         65                  70                  75                  80
Xaa Leu Pro Glu Glu Gln Asp Gln Asn Tyr Val Cys Lys His Thr Tyr
                    85                  90                  95
Val Asp Arg Gly Trp Gly Asn Gly Cys Gly Leu Phe Gly Lys Gly Ser
                100                 105                 110
Leu Val Thr Cys Ala Lys Phe Gln Cys Leu Glu Pro Ile Glu Gly Lys
                115                 120                 125
Val Val Gln Tyr Glu Asn Leu Lys Tyr Thr Val Ile Ile Thr Val His
            130                 135                 140
Thr Gly Asp Gln His Gln Val Gly Asn Glu Thr Gln Gly Val Thr Ala
145                 150                 155                 160
Glu Ile Thr Pro Gln Ala Ser Thr Thr Glu Ala Ile Leu Pro Glu Tyr
                    165                 170                 175
Gly Thr Leu Gly Leu Glu Cys Ser Pro Arg Thr Gly Leu Asp Phe Asn
                180                 185                 190
Glu Met Ile Leu Leu Thr Met Lys Asn Lys Ala Trp Met Val His Arg
                195                 200                 205
Gln Trp Phe Phe Asp Leu Pro Leu Pro Trp Thr Ser Gly Ala Thr Thr
            210                 215                 220
Glu Thr Pro Thr Trp Asn Arg Lys Glu Leu Leu Val Thr Phe Lys Asn
225                 230                 235                 240
Ala His Ala Lys Lys Gln Glu Val Val Val Leu Gly Ser Gln Glu Gly
                    245                 250                 255
Ala Met His Thr Ala Leu Thr Gly Ala Thr Glu Ile Gln Asn Ser Gly
                260                 265                 270
Gly Thr Ser Ile Phe Ala Gly His Leu Lys Cys Arg Leu Lys Met Asp
            275                 280                 285
Lys Leu Glu Leu Lys Gly Met Ser Tyr Ala Met Cys Thr Asn Thr Phe
            290                 295                 300
Val Leu Lys Lys Glu Val Ser Glu Thr Gln His Gly Thr Ile Leu Ile
305                 310                 315                 320
Lys Val Glu Tyr Lys Gly Glu Asp Xaa Pro Cys Lys Ile Pro Phe Ser
                    325                 330                 335
Thr Glu Asp Gly Gln Gly Lys Ala His Asn Gly Arg Leu Ile Thr Ala
                340                 345                 350
Asn Pro Val Val Thr Lys Lys Glu Glu Pro Val Asn Ile Glu Ala Glu
                355                 360                 365
Pro Pro Phe Gly Glu Ser Asn Ile Val Ile Gly Ile Gly Asp Asn Ala
            370                 375                 380
Leu Lys Ile Asn Trp Tyr Lys Lys Gly Ser Ser Ile Gly Lys Met Phe
385                 390                 395                 400
Glu Ala Thr Ala Arg Gly Ala Arg Arg Met Ala Ile Leu Gly Asp Thr
                    405                 410                 415
Ala Trp Asp Phe Gly Ser Val Gly Gly Val Leu Asn Ser Leu Gly Lys
                420                 425                 430
Met Val His Gln Ile Phe Gly Ser Ala Tyr Thr Ala Leu Phe Ser Gly
            435                 440                 445
Val Ser Trp Val Met Lys Ile Gly Ile Gly Val Leu Leu Thr Trp Ile
            450                 455                 460
Gly Leu Asn Ser Lys Asn Thr Ser Met Ser Phe Ser Cys Ile Ala Ile
465                 470                 475                 480
Gly Ile Ile Thr Leu Tyr Leu Gly Ala Val Val Gln Ala
                    485                 490
```

<210> SEQ ID NO 5
<211> LENGTH: 495
<212> TYPE: PRT
<213> ORGANISM: Flavivirus dengue virus

<400> SEQUENCE: 5

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Gln Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Val Ile
            340                 345                 350

Ser Ser Thr Pro Leu Ala Glu Asn Thr Asn Ser Val Thr Asn Ile Glu
        355                 360                 365

Leu Glu Pro Pro Phe Gly Asp Ser Tyr Ile Val Ile Gly Val Gly Asn

-continued

```
             370                 375                 380
Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
                420                 425                 430

Gly Lys Ala Val His Gln Val Phe Gly Ser Val Tyr Thr Thr Met Phe
            435                 440                 445

Gly Gly Val Ser Trp Met Ile Arg Ile Leu Ile Gly Phe Leu Val Leu
        450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495
```